United States Patent [19]

Fitzky et al.

[11] 4,270,083
[45] May 26, 1981

[54] MICROWAVE MOISTURE MEASURING INSTRUMENT WITH SWITCHABLE MEASURING REGIONS

[75] Inventors: Hans G. Fitzky, Odenthal; Jörg M. Söder; Franz Schmitt, both of Cologne; Norbert Bollongino, Leichlingen; Helmut Rehrmann, Leverkusen, all of Fed. Rep. of Germany

[73] Assignee: Bayer Aktiengesellschaft, Leverkusen, Fed. Rep. of Germany

[21] Appl. No.: 90,372

[22] Filed: Nov. 1, 1979

[30] Foreign Application Priority Data

Nov. 11, 1978 [DE] Fed. Rep. of Germany ....... 2848993

[51] Int. Cl.³ ............................................. G01R 27/04
[52] U.S. Cl. ................................................ 324/58.5 C
[58] Field of Search ............... 324/58.5 C, 58 C, 58 R

[56] References Cited

U.S. PATENT DOCUMENTS

| | | | |
|---|---|---|---|
| 3,883,798 | 5/1975 | Free | 324/58.5 C |
| 3,946,308 | 3/1976 | Miura et al. | 324/58.5 C |
| 4,050,015 | 9/1977 | Zollner | 324/58.5 C |
| 4,203,067 | 5/1980 | Fitzky et al. | 324/58.5 C |

Primary Examiner—Stanley T. Krawczewicz
Attorney, Agent, or Firm—Sprung, Felfe, Horn, Lynch & Kramer

[57] ABSTRACT

The generator for the microwave measuring arrangement consists of a frequency-modulated oscillator which feeds a cavity measuring resonator in a transmission arrangement. The sample to be examined is located in the center of the resonator. The microwave signal allowed through the resonator is detected as the peak amplitude of a detector circuit, the change in the signal corresponding to the change in the quality factor due to the presence of the sample introduced. The average frequency of the microwave oscillator can be switched over several stages in order to expand the range of measurement. Each time the frequency is switched over, a different field mode is excited in the measuring resonator so that the sample is located in a mode region of the electrical measuring field for measuring high water contents and in a maximum of the electrical measuring field for measuring low water contents.

16 Claims, 6 Drawing Figures

MICROWAVE MOISTURE MEASURING INSTRUMENT WITH SWITCHABLE MEASURING REGIONS

BACKGROUND OF THE INVENTION

The invention relates to an apparatus for measuring the water content of electrically non-conductive, isotropic materials, in particular of powders, granules, pastes and liquids, consisting of a frequency-modulated microwave oscillator which, in a transmission arrangement, feeds a cavity measuring resonator which is charged with the sample and a detector circuit for measuring the peak amplitude of the transmission signal, the change of which corresponds to the change in the quality factor due to the sample introduced.

Instruments of this type are known and are used to rapidly determine the moisture of products in the laboratory and factory. A survey of the prior art is given, for example, in HG Fitzky, GIT Fachz. Lab. 1974, page 869 et seq. This document describes, among other things, a measuring instrument for measuring the moisture of individual samples in the laboratory on the basis of a cylindrical measuring resonator with the $TM_{010}$ field mode. In this arrangement, a sample container made of Teflon (Registered Trade Mark), containing the sample to be examined, is inserted along the axial direction. In order to achieve high sensitivity of measurement, the sample is located at the position of the maximum-electric field inside the resonator. The resonator is designed as a transmission cell, the connection and disconnection being effected by magnetic iris couplers. The diameter and depth of the round iris passage, for example on two opposing points of the cylindrical resonator wall, determine the quality factor Q of the resonator ($Q=\omega/\Delta\omega, \omega$=mean frequency, $\Delta\omega$=bandwidth at the half-power points at resonance) and thus the sensitivity. A high quality factor denotes a large number of radiation traverses of the sample and thus high sensitivity of measurement and visa versa. Small iris passage diameters produce weak coupling and thus a high resonator quality factor, large diameters for the iris passage produce marked coupling and a low quality factor. Conventional instruments are determined with respect to the range of moisture measurement by the choice of the diameter of the iris passage. Instruments of this type have the disadvantage that they only supply accurate results within a narrowly restricted range of moisture, for example, within 0.5 to 5% by weight of $H_2O$. The iris passage is not switched over mechanically due to difficult problems associated with contact. If measurements are required over a wider range of moisture content, it is necessary to use several instruments for differing ranges of measurement. Correspondingly smaller weighed quantities can be used as an alternative, for example, a charge of only one tenth of the quantity normally used is required (0.5 g instead of 5 g), if the moisture content is ten times higher. The disadvantages of this process is that variations can falsify the test result if the product is not completely homogeneous or if the granulation of the material does not allow simple division.

SUMMARY OF THE INVENTION

An object of the invention is to develop a moisture measuring instrument which allows moisture measurement over a wide range of moisture content in a simple and absolutely reproducible manner (calibratable), two or more moisture measuring ranges being produced by means of electrical switching.

According to the present invention there is provided an apparatus for measuring the water content of a sample of an electrically non-conductive isotropic material in a sample container, comprising a frequency-modulated microwave oscillator which supplies a cavity measuring resonator in a transmission arrangement, which resonator is adapted to be loaded in the centre with the sample container, and a detector circuit for measuring the peak amplitude of a transmission signal, a change of which corresponds to the change in the quality factor caused by the sample introduced, wherein the apparatus is adapted so that the mean frequency of the microwave oscillator can be switched over in several steps and a different field mode is excited in the resonator during each switch over in order that the sample is located in a mode region of the electrical measuring field for measuring high water content and in a maximum of the electrical measuring field for measuring low water contents.

In a preferred embodiment of the invention, the resonator quality factor can also be adjusted by switching to various coupling members on the resonator input and output. This gives rise another method of adapting the measuring region of the instrument according to the respective problems established in practice.

Advantages of the invention lie in the fact that only a single instrument is needed for all moisture measuring regions occurring in practice. The measuring region can be switched over on the instrument itself in a simple manner.

The fittings which were previously needed on the instrument can be dispensed with by using various couplers and optionally also sample holders when the measuring region is changed. In the design with periodic scanning of the resonance signals of the various excited modes of field, the optimum measuring range is even adjusted automatically by the instrument for the respective measured value of moisture.

BRIEF DESCRIPTION OF THE DRAWINGS

An embodiment of the invention is described in more detail below with reference to the accompanying drawings. In the drawings.

DETAILED DESCRIPTION OF THE INVENTION

The invention is based on two important facts:

1. The damping of a cavity resonator by a specific quantity (weighed-in quantity) of a substance which is liable to electrical losses, of a specific shape (sample container) depends quite substantially on the point at which the sample is introduced for a given field mode. It is assumed that the field distribution is not disturbed too much by the sample introduced and that the sample is located in a region with an approximately homogeneous field distribution so that small changes of the position and nonhomogeneities within the sample do not produce a disturbing variation in the damping value. The sample whose moisture is to be measured is usually brought into the region of the electrical field antimode so as to obtain high sensitivity of measurement for small water contents. With high water contents, the resulting damping is usually too great to allow accurate measurement. This can be remedied by reducing the quality factor of the resonator (reducing the number of radiation traverses of the sample) or by reducing the quantity weighed in, but these solutions are accompanied by the disadvantages described above.

Tests have shown that it is however also possible to utilize the normal quantity of very moist material for measuring purposes if the sample is placed not at the position of the electrical field antimode but rather in the region of the mode of the electrical field, which is at the same time the antimode of the magnetic field. The surprising result measured showed that a water concentration of up to 20 times higher can be detected when using conventional quantities of sample.

In order to broaden the measuring region of a measuring resonator, the sample could be converted from the region of the E-maximum to the region of the E-minimum. The measuring resonator would then have to be provided with two or possibly more take-up points for the sample container. By contrast, the electric switching according to the invention of the field mode represents a much more elegant solution. It is sufficient to use a single take-up point for the sample container as this circuit enables the electrical field to be shifted from the E-field maximum to the E-field minimum at the sample location.

2. The sensitivity of the instrument for measuring moisture can also be influenced by the quality factor of the measuring resonator. The quality factor (in the case of very weak coupling) generally increases towards higher field modes, say in the order $TE_{101}$, $TE_{102}$, $TE_{103}$ etc. If the resonator input and output are coupled very strongly, the quality factor (approximately equal to the number of radiation traverses of the sample) can be varied by the choice of position and dimensioning of an electric coupling element.

Figure 1:
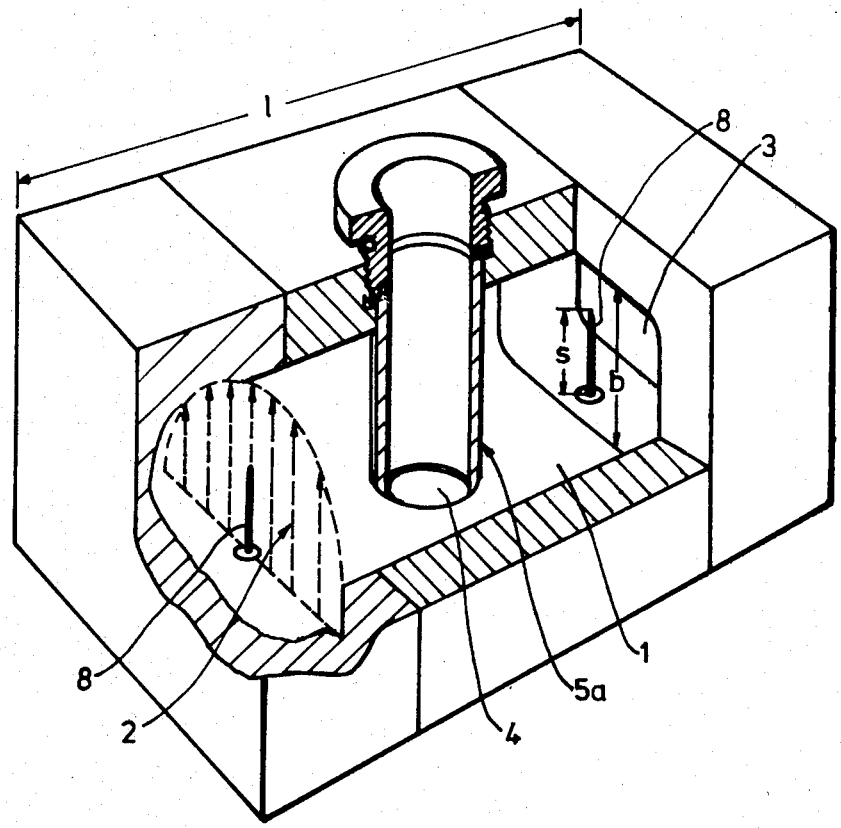
FIG. 1 shows a measuring resonator with electrical coupling.
Figure 2:
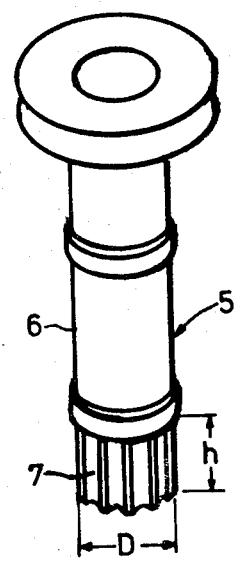
FIG. 2 shows an associated sample container.
Figure 3:
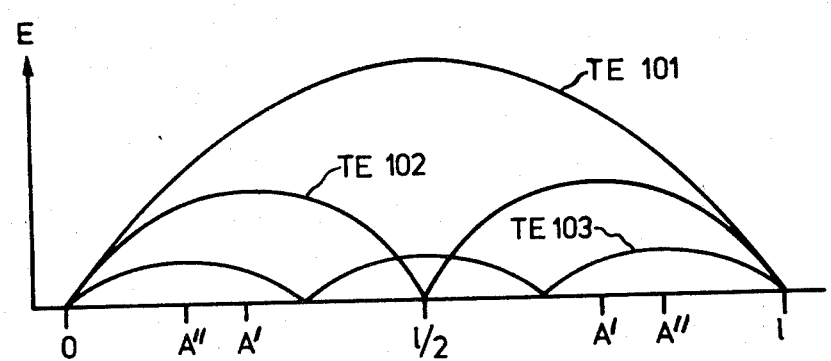
FIG. 3 shows the electrical field distribution along the central line of the resonator for various field modes.

A measuring resonator with electric coupling is indicated in the FIG. 1. It can be excited in the field modes $TE_{101}$ and $TE_{102}$. The actual resonator comprises a rectangular cavity 1 which is surrounded by metal and has a resonator input 2 and the resonator output 3. Cylindrical openings 4 are located on the upper and lower sides of the resonator for insertion of a sample container 5 (see FIG. 2). The sample container 5 comprises hollow cylinder 6 made of polytetrafluoroethylene or a material with similarly low dielectric losses and a minimum of water absorbency. In order to restrict the sample volume to a region of an approximately constant measuring field, the diameter D of the hollow cylinder is selected smaller than 20% of the length of the pipe wavelength of the highest frequency field mode and the height h of the cylindrical sample chamber is selected smaller than 30% of the height b of the rectangular wave guide. In the range of low moistures, nonhomogeneous partial waves, for example $TM_{01}$ or $TM_{11}$ mode, must be avoided in the sample chamber 7. An abnormal course of the calibration curve would otherwise be produced. For this purpose, the diameter D of the sample chamber 7 would have to be restricted in such a way that $D \leq (1/\sqrt{\epsilon'})d_g$, in which $\epsilon'$ represents the real part of the dielectric constant of the sample and $d_g = k_\nu \lambda$ with $k_\nu = 0.766$ for the $TM_{01}$ wave and $k_\nu = 0.586$ for the $TM_{11}$ wave. $\lambda$ is the wavelength in a vacuum. D generally ranges from 10 to 40 mm. The sample container 5 is inserted from the top into a PTFE guide tube 5a in the centre of the resonator 1. The sample chamber 7 is then located in the centre of the resonator 1. When the $TE_{101}$ field mode is excited, the sample is located in the E-field maximum, while it is located in the region of the minimum during excitation in the $TE_{102}$ field mode (see FIG. 3). In the first case, high measurement sensitivity to moisture is achieved while in the second case the sensitivity to measurement is lower by a factor of from 10 to 20. An additonal moisture measuring region of average sensitivity to measurement can be developed by using the $TE_{103}$ field mode, as described in more detail below. The frequency ranges of the three field modes are sufficiently separated so as to avoid an overlap (in the case of variable detuning by differing real parts of the dielectric constant of the samples). In a typical design, for example, the following operating resonance frequencies are produced once the empty sample container 5 is inserted:

with $TE_{101}$-field mode $f_0 = 1.93$ GHz,
with $TE_{102}$-field mode $f_0 = 2.51$ GHz and
with $TE_{103}$-field mode $f_0 = 2.98$ GHz.

When the sample container is filled, an additional frequency shift by a maximum of 200 MHz takes place to lower values.

The resonator is coupled electrically via small rod aerials 8 to the resonator input 2 and output 3. As described above, the quality factor of the resonator can be influenced by the choice of location and length of the rod aerials 8. It is important for the quality factors pertaining to the individual field modes to be selected so as to achieve, on the one hand, the desired gradation in the moisture measuring ranges and, on the other hand, suppression of undesirable field modes. In practice, several rod aerials 8 each are arranged on the resonator input and the resonator output parallel to the E-vector along the central line 9 and can be connected to the microwave oscillator. If both the $TE_{101}$ and $TE_{102}$ field modes are used, efforts will be made to raise the quality factor in the $TE_{101}$ field mode to be sufficiently high to obtain a high sensitivity to measurement (measurement in the E-field maximum) so as to allow low moisture values to be measured. This is only possible with a weak coupling. A weak coupling is achieved by means of a relatively short aerial length S, i.e. $0 \leq S \leq \lambda/4$. The position of the rod aerials 8 is obtained from correlating the requirement of a low sensitivity to measurement (small quality factor) with the $TE_{102}$ field mode and thus a location in the E-maximum of the $TE_{102}$ field mode taking into consideration a slight distortion of field owing to the sample introduced. With electrical connection and disconnection, the $TE_{103}$ field mode is suitable for obtaining an even higher sensitivity to measurement than that obtained when using $TE_{101}$ field mode. In this case, the aerial position A" should be adopted instead of A', A" corresponding to the E-field maximum of the $TE_{103}$ field type (see FIG. 3). This prevents ambiguity in the display. When the resonator 1 is loaded with the empty sample container, the following quality factors result, for example, for the individual field modes:

$TE_{101}$ Q = 690, coupling at A', A', S = 10 mm $TE_{102}$ Q=285, coupling at A', A', S=10 mm
$TE_{103}$ Q=1355, coupling at A', A', S=10 mm Under these conditions, a measuring range of about 0.5 to 10% by weight can be produced when using the $TE_{101}$ field mode and a measuring range of 10 to almost 100% water content can be produced with the $TE_{102}$ field mode.

Figure 4:
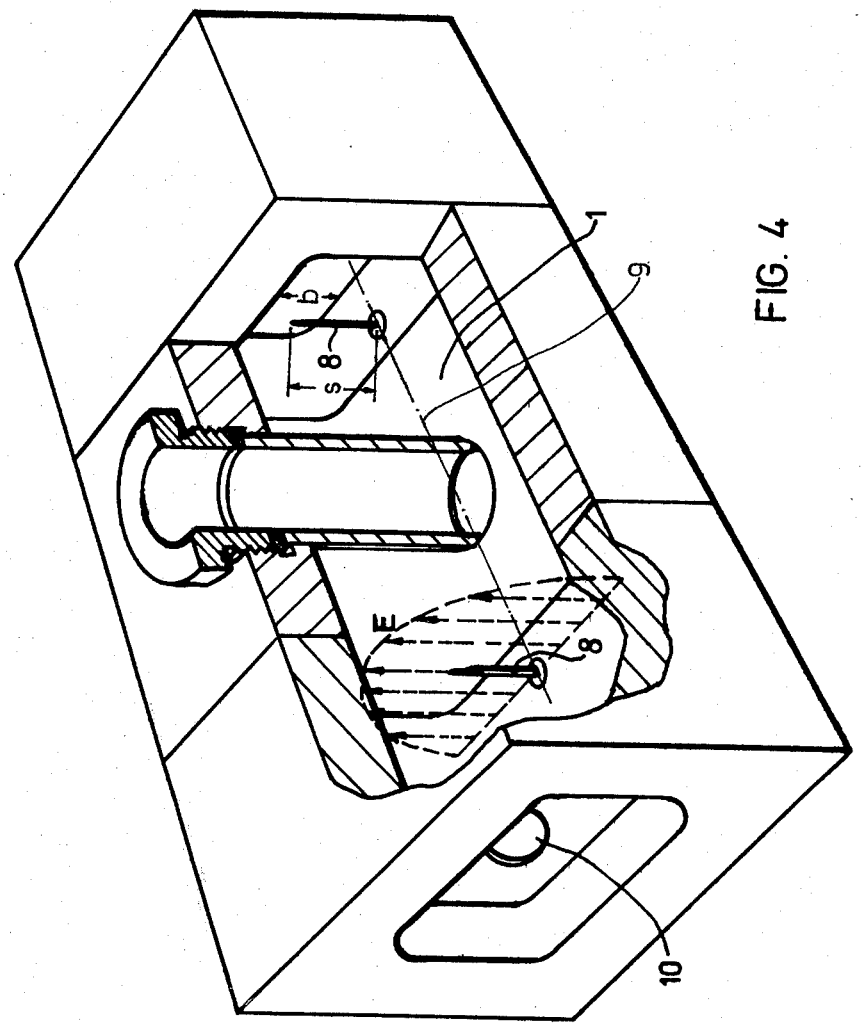
FIG. 4 shows a measuring resonator with magnetic coupling.

It is possible to provide a purely magnetic coupling using iris diaphragms 10 instead of electrical coupling in and coupling out of the microwave energy with the aid of rod aerials (see FIG. 4, the rod aerials 8 are also drawn in in this embodiment). The quality factor is determined in this case by suitable choice of the diameter and depth of the iris passage. The magnetic coupling allows better suppression of interfering field modes in higher frequency ranges and therefore allows the use of higher field modes of up to say $TE_{105}$. In addition, better gradation of the moisture measuring ranges can be achieved. Thus, the coupling of the $TE_{101}$ field mode can be reduced considerably by raising the lower frequency limit of the adapter into the region of the $TE_{101}$ resonance when using coaxial-tubular conductors (adapters), so that a very weak coupling is produced for the $TE_{101}$ field mode but a very strong coupling which increases with the frequency is produced for the $TE_{102}$ and higher field modes.

The sequence of field modes in order of decreasing sensitivity to the measurement of moisture then reads $TE_{101}$, $TE_{103}$, $TE_{105}$, $TE_{104}$, $TE_{102}$.

When an odd number of halfwaves is excited, the sample is located in the E-field maximum. If, however, the sample is arranged in the H-field maximum, a nonhomogeneous partial wave can be excited in the sample volume if the sample container 5 is suitably dimensioned. Thus, for example, the $TM_{010}$ wave can be excited at $D=0.766\lambda/\sqrt{\epsilon'}$ or the $TE_{11}$ wave at $D=0.586\lambda/\sqrt{\epsilon'}$, for example, by magnetic coupling from the $TE_{102}$ field mode prevailing in the rectangular resonator in the cylindrical sample volume (sample in the centre of the resonator, cylinder axis parallel to the E-field of the $TE_{102}$ field mode). In these equations, D = the diameter of the sample volume, $\epsilon'$ = the real part of the dielectric constant and represents the wavelength in a vacuum. Parasitic resonances in the sample volume are normally undesirable as they can interfere with the monotonic path of the calibration curve. They cause abnormally high absorptions to occur at certain water contents which yield an $\epsilon'$ value required for resonance. This increase in the absorption can however be used to make the calibration curve linear at the upper end of the moisture measurement range, i.e. with very high water contents. High sensitivity of measurement is also achieved in this range in this way.

Figure 5:
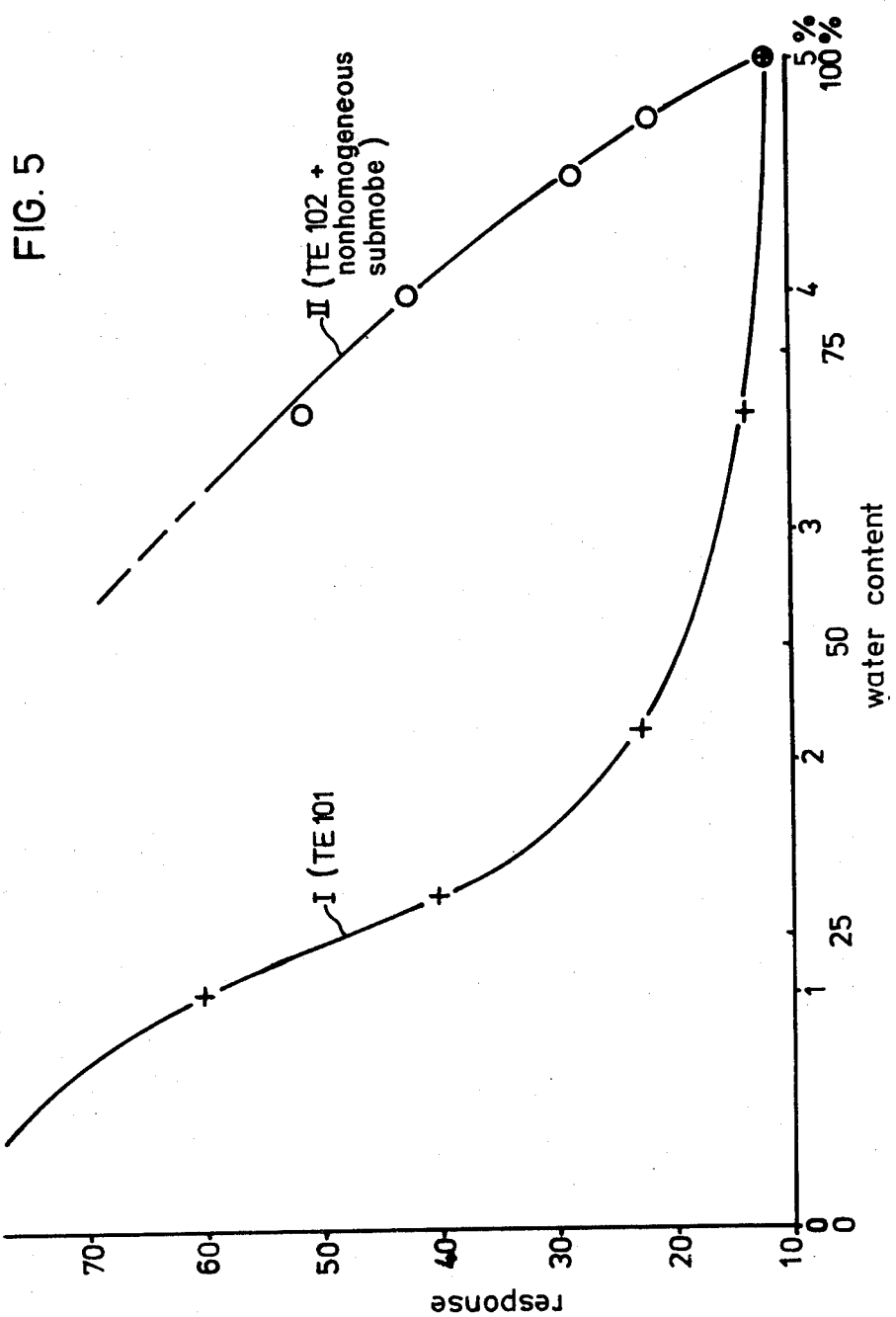
FIG. 5 shows calibration curves for the instrument with and without excitation of an inhomogeneous partial wave in the sample volume.

FIG. 5 shows the path of the calibration curve produced when a nonhomogeneous partial wave is employed without and with excitation in the sample volume. The curve I was measured for the $TE_{101}$ field mode without excitation of a nonhomogeneous partial wave, while the calibration curve II was produced with the $TE_{102}$ field mode and during excitation of a nonhomogeneous partial wave in the sample volume. It is observed that the accuracy of measurement is substantially increased in the upper portion of the measuring range relative to I by exciting a nonhomogeneous partial wave when the water content of the sample is high. Curve I has a very flat path in this portion.

In practice, the calibration curve II is produced by dimensioning the diameter D of the sample container 5 to correspond to the above-mentioned critical conditions. These conditions obviously apply only to the high water content at the upper end of the range of measurement.

Figure 6:
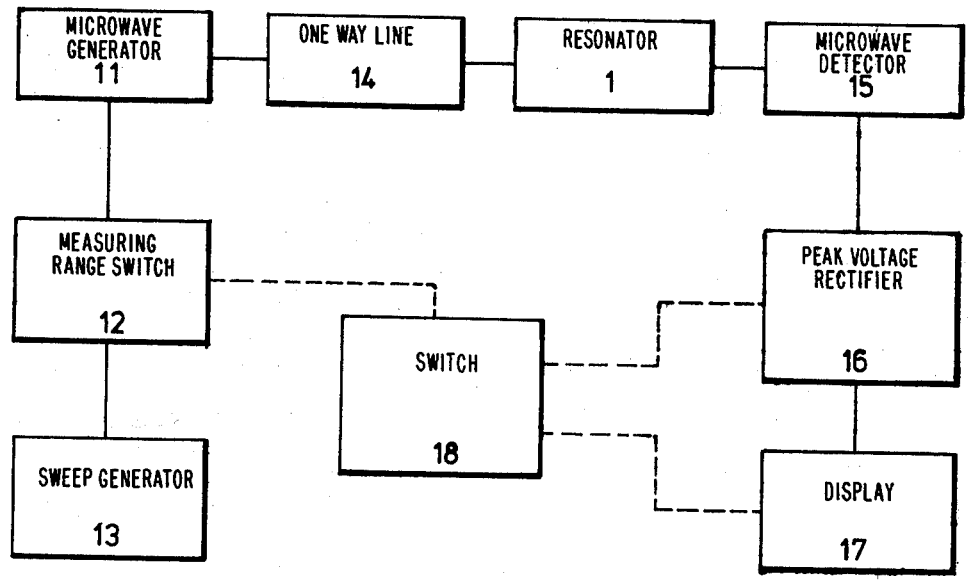
FIG. 6 shows a block circuit diagram of the complete microwave measuring arrangement.

The complete microwave measuring arrangement is illustrated with reference to the block diagram, FIG. 6. The microwave generator comprises a transistor oscillator 11 which can be coordinated with the aid of a varactor. The fundamental voltage is selected beforehand by means of the measuring range switch 12 and the oscillator 11 is thus coordinated to the average frequency of the respective natural resonance, for example 1.9, 2.5 or 3 GHz. At higher frequencies, it is preferable to use a so-called Gunn oscillator, the frequency of which can be varied over an octave band, for example, by means of a tuning diode (varactor). The fundamental voltage is superimposed by a saw tooth shaped sweep voltage from the sweep generator 13 with a lower amplitude. The oscillator frequency is thus frequency modulated periodically with a stroke of, for example, 200 MHz, so that the complete resonance curve of the respective natural resonance, for example $TE_{101}$ or $TE_{102}$ or $TE_{103}$ etc. is exceeded whenever the measuring resonator 1 is loaded with the empty and filled sample container 5. A one way line 14 is connected between the measuring resonator 1 and oscillator 11 to prevent the reactive load from acting on the oscillator 11. The microwave detector 15, which delivers the resonance curve of the measuring resonator 1 after rectification of the microwave signal is connected at the output of the measuring resonator 1. The one way line 14 and the detector 15 can be connected selectively to the rod aerials 8 and iris couplers 9 provided in the measuring resonator.

The peak voltage value at the microwave detector 15 is determined in a subsequent peak voltage rectifier 16. The magnitude of the peak voltage value represents a monotonic function of the moisture content of the sample and is portrayed digitally or analogously by the display 17 in the form of the so-called moisture value. The moisture value can be converted into percentages by weight moisture with the aid of the calibration curve.

In a modified embodiment, the measuring range is not switched over manually but automatically and periodically. In this design, the measuring signal is electronically by switch 18 allocated to various measuring channels which correspond to the individual moisture measuring ranges. In this manner, the measuring channel is automatically selected with the corresponding moisture measuring range, in which the measured value lies at any time. The instrument does not therefore need to be adjusted manually to the correct range of measurement.

We claim:

1. An apparatus for measuring the water content of a sample of an electrically non-conductive isotropic material, comprising means for producing a frequency modulated microwave signal, a sample container, a cavity measuring resonator receptive of the microwave signal in a transmission arrangement and configured to be loaded in the centre thereof with the sample container, a detector circuit for measuring the peak amplitude of the transmission signal from the resonator a change of which corresponds to a change in the quality factor caused by the sample introduced and means for switching over the mean frequency of the microwave oscillator in several steps to excite the resonator in a different field mode during each switch over thereby locating the sample in a mode region of the electrical measuring field for measuring high water content and in a maximum of the electrical measuring field for measuring low water contents.

2. An apparatus according to claim 1, further comprising means for adjusting the resonator quality factor including means for switching the microwave energy to a plurality of coupling members at the resonator input and resonator output.

3. An apparatus according to claim 1 or 2, wherein the range of frequency steps of the microwave signal is such that the complete resonance curve of the resonator loaded with an empty and a filled sample container is exceeded and the mean frequencies of the microwave signal are selected such that the frequency ranges of the individual field modes which are produced during loading with the empty and the filled sample container do not overlap.

4. An apparatus according to claim 1, wherein the mean frequency of the microwave signal is switched over in several stages in the range of from 0.5 and 18 GHz, the frequency step is selected from the range of from 10 to 1000 MHz and the modulation frequency from the range of from 1 Hz to 100 kHz and the measuring resonator is a rectangular cavity resonator which can be excited in one of both the $TE_{101}$ and in the $TE_{102}$ field modes, the $TE_{102}$ and the $TE_{103}$ field modes, the $TE_{101}$, $Te_{102}$ and $TE_{103}$ modes and in any mode combination up to the $TE_{105}$ field mode.

5. An apparatus according to claim 1, further comprising means for coupling microwave energy into and out of the resonator comprising rod aerials orientated parallel to the E-vector having a length up to $\lambda/4$, $\lambda$ representing the wavelength of the shortest operating wavelength.

6. An apparatus according to claim 5, wherein the resonator is a rectangular cavity resonator and wherein the rod aerials are arranged along the central line of the breadth of the rectangular symetrically with respect to the centre of the resonator between the end of the resonator and the outer E-field maximum of the highest field mode used and the microwave signal is switchable between a plurality of couplers in order to adjust the quality factor with the respective field mode used.

7. An apparatus according to claim 1, wherein the resonator is a rectangular cavity resonator and further comprising magnetic iris couplers arranged in the centre of both end cross-sections of the cavity to couple microwave energy into and out of the cavity resonator.

8. An apparatus according to claim 7, wherein coaxial-tubular conductor adapters are provided for coupling coaxially supplied microwave energy, said adapters having a long-wave critical frequency selected sufficiently high for the degree of coupling to increase from the lowest frequency adjusted for the $TE_{101}$ field mode to the higher frequencies and consequently to obtain a gradation of the quality factors of $Q_{TE101} > Q_{TE103} > Q_{TE102}$ with the resonator loaded with an empty sample container.

9. An apparatus according to claim 1, wherein the resonator is a rectangular cavity resonator having an opening in the centre which serves to take up and guide the sample container parallel to the E-vector of the $TE_{101}$ field mode.

10. An apparatus according to claim 1, further comprising a circuit for periodically scanning the peak voltage values of the resonance signals of the various signals of the various excited field modes and including a gate control synchronized for emission of the measured signal in a corresponding measuring channel.

11. An apparatus according to claim 1, wherein the sample container comprises a hollow cylinder made of a material having a low dielectric losses and a minimum of water absorbency, and the diameter of the sample chamber is smaller than 20% of the pipe wavelength of the highest frequency field mode and the height of the sample chamber is smaller than 30% of the smaller cross sectional dimension of the rectangular pipe cross-section.

12. An apparatus according to claim 11 wherein said material of the hollow cylinder is poly-tetrafluoroethylene.

13. An apparatus according to claim 11, wherein the diameter of the sample chamber is smaller than $(1/\sqrt{\epsilon'})d_g$, wherein $\epsilon'$ = real part of the dielectric constant of the sample and $d_g = k_\nu \lambda$ wherein $k_\nu = 0.766$ for the $TM_{01}$ wave and $k_\nu = 0.586$ for the $TM_{11}$ wave.

14. An apparatus according to claim 11 wherein the diameter D of the sample chamber is selected in accordance with $D = 0.766 \lambda/\sqrt{\epsilon'}$, so that, in the sample volume, with the nonhomogeneous partial wave of the $TE_{010}$ field mode is achieved with high water contents (60 to 100%), $\epsilon'$ representing the maximum value of the real part of the dielectric constant of the sample with a maximum water content and $\lambda$ representing the wavelength in a vacuum.

15. An apparatus according to claim 1 wherein the resonator is a rectangular resonator and the width a of the rectangular resonator is selected sufficiently large for a tubular wavelength of $\lambda/2 = a$ to be adjustable for obtaining a measuring field which is as homogeneous as possible.

16. An apparatus according to claim 1 wherein said electrically non-conductive isotropic material comprises a powder, granulate, paste or liquid.

* * * * *